United States Patent
Scott et al.

(10) Patent No.: US 11,464,951 B1
(45) Date of Patent: Oct. 11, 2022

(54) APPARATUS TO COUPLE A DRAINAGE RESERVOIR TO A BODY OF A PATIENT

(71) Applicants: Shannon Scott, Centerville, MN (US); James L. Scott, Centerville, MN (US)

(72) Inventors: Shannon Scott, Centerville, MN (US); James L. Scott, Centerville, MN (US)

(*) Notice: Subject to any disclaimer, the term of this patent is extended or adjusted under 35 U.S.C. 154(b) by 242 days.

(21) Appl. No.: 16/193,846

(22) Filed: Nov. 16, 2018

(51) Int. Cl.
| | |
|---|---|
| A61M 27/00 | (2006.01) |
| A61M 1/00 | (2006.01) |
| A61M 31/00 | (2006.01) |
| B67C 3/16 | (2006.01) |
| B65B 1/04 | (2006.01) |
| B65B 31/04 | (2006.01) |

(52) U.S. Cl.
CPC ....... *A61M 27/00* (2013.01); *A61M 2209/088* (2013.01)

(58) Field of Classification Search
CPC ........ A61M 27/00; A61M 1/00; A61M 31/00; A61M 37/00; A61M 2209/088; B67C 3/16; B65B 1/04; B65B 31/04
See application file for complete search history.

(56) References Cited

U.S. PATENT DOCUMENTS

| | | | | |
|---|---|---|---|---|
| 5,573,152 A | * | 11/1996 | Arnold | B65D 23/003 224/249 |
| 7,927,311 B1 | * | 4/2011 | Bachelder | A45F 5/00 604/179 |
| 8,066,657 B2 | | 11/2011 | Frazer | |
| 9,581,292 B2 | * | 2/2017 | Kremer | F16B 45/00 |
| 2003/0111496 A1 | * | 6/2003 | Abbott | F16B 45/02 224/148.6 |
| 2011/0178466 A1 | * | 7/2011 | Vioreanu | A61M 25/02 604/180 |
| 2016/0255918 A1 | * | 9/2016 | Grossman | F16B 45/02 |

FOREIGN PATENT DOCUMENTS

JP  2018202200 A  *  4/2012

OTHER PUBLICATIONS

Collins English Dictionary—Complete and Unabridged, 12th Edition 2014 (Year: 2014).*

* cited by examiner

*Primary Examiner* — Tatyana Zalukaeva
*Assistant Examiner* — Ilya Y Treyger
(74) *Attorney, Agent, or Firm* — Sanchelima & Associates, P.A.; Christian Sanchelima; Jesus Sanchelima

(57) ABSTRACT

An apparatus to couple a drainage reservoir to a patient is disclosed. The apparatus comprises a device having, a first end, a second end, and a tab with an orifice. The first end comprises an adhesive surface. Further, the apparatus includes a clip attached to the orifice in the tab of the device. The first end of the device is attached to the body of the patient, and the clip is coupled to the strap on the drainage reservoir such that the drainage reservoir is coupled to the body of the patient with the help of the device and the included clip.

12 Claims, 4 Drawing Sheets

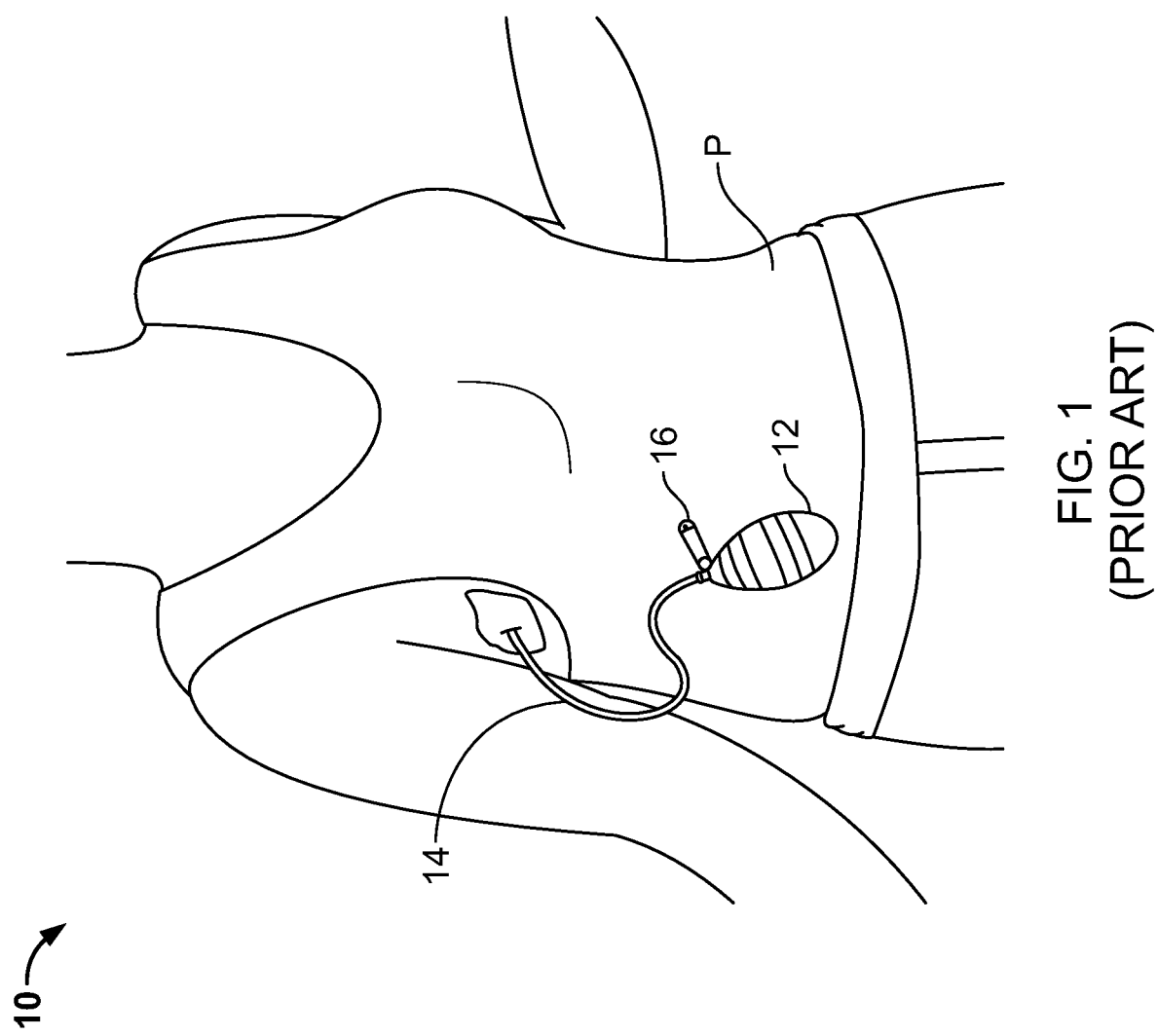

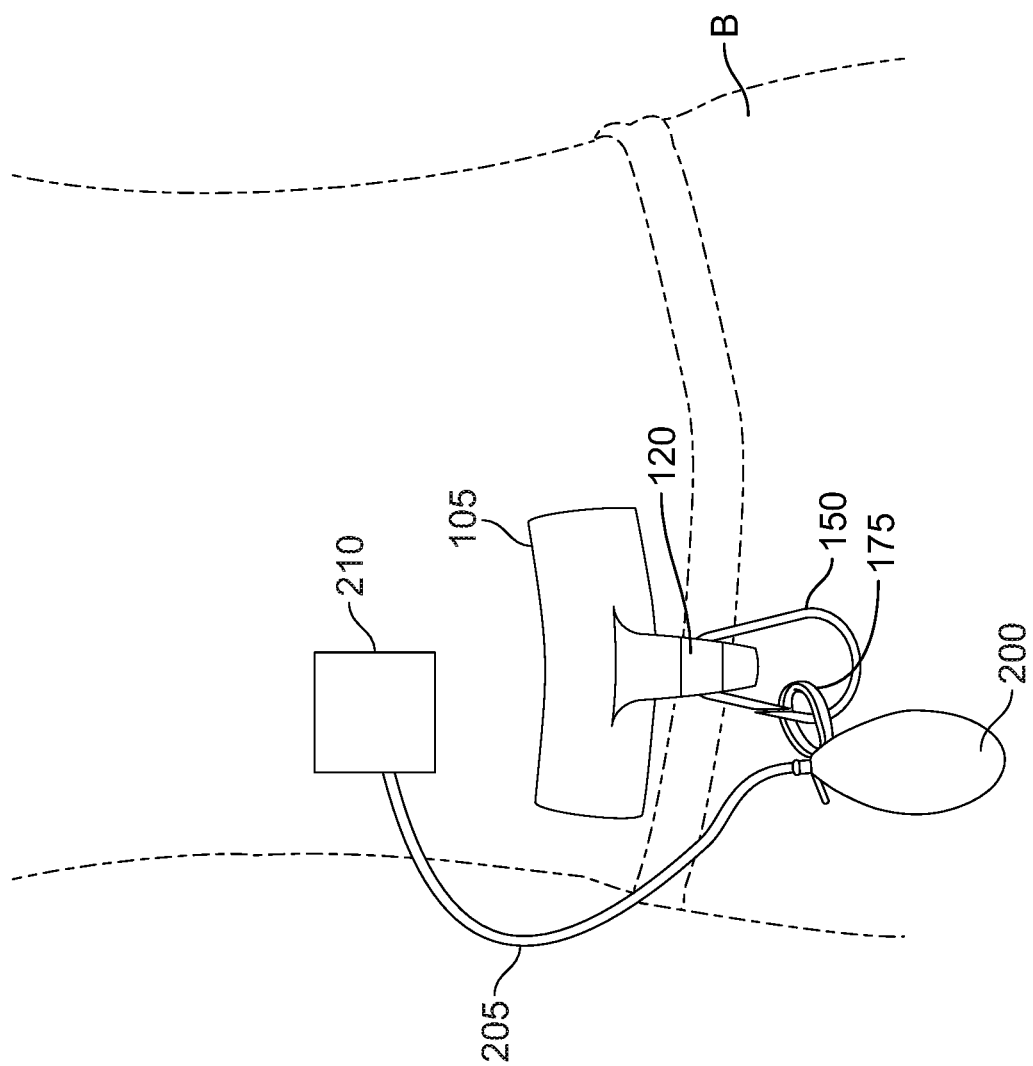

APPARATUS TO COUPLE A DRAINAGE RESERVOIR TO A BODY OF A PATIENT

BACKGROUND OF THE INVENTION

1. Field of the Invention

The present disclosure generally relates to the field of medical devices. More specifically, the present disclosure relates to an apparatus for protecting and coupling post-operative drainage systems to a patient.

2. Description of the Related Art

It is known that patients may undergo variety of surgeries. The surgeries may include, but not limited to, an abdominal surgery, a breast surgery, a craniotomy and so on. After performing the surgery, a physician may provide a drain device, which is attached to a body of the patient.

The drain device comprises a drainage tube in which one end is secured to the body of the patient. The other end of the drainage tube is connected to a drainage reservoir. The drainage reservoir may include a Jackson-Pratt drain or drain bulb or drainage bulb. Typically, the drainage reservoir is provided in an oval or in an egg shape.

Typically, the drainage reservoir is secured to hospital gowns or clothing using a safety pin. Referring to FIG. 1, an example of a bulb type (Jackson Pratt) drain device 10 employed in post-operative recovery procedures is shown, in accordance with prior art. As explained above, the drain device 10 comprises a drainage reservoir 12, a drainage tube 14. As can be seen, the drainage reservoir 12 is coupled to a patient P using a pin or safety pin 16. The drainage reservoir 12 is generally provided to carry fluids away from surgical sites. The drainage reservoir 12 is provided to prevent fluid such as blood build-up in a closed space, which may cause either disruption of the wound and the healing process or become an infected abscess.

However, the drain device 10 needs to be placed for several days to weeks. As explained above, the drain device 10 is typically secured to the hospital gowns or clothing using the safety pin 16. It should be understood that the safety pin 16 might cause puncture in the drainage tube 14. In addition, the safety pin 16 may puncture the patient P. Further, the patient P may have to take support of other individuals while holding the drain bulb as there is no way to attach or safety pin the device while showering. Without other individuals, the patient P may struggle to hold the drainage reservoir 12 and take shower.

In addition, any movement by the patient P may twist or move the drainage reservoir 12, which might result in pulling the drain tube out of the wound and loose the suction required to receive the blood into the drainage reservoir 12. The patient P may have to push back the drain tube into the wound and the drainage reservoir 12 may have to be reset to recreate the suction.

Several attempts were made in the past to hold the drainage reservoir. One such example was disclosed in a United States granted U.S. Pat. No. 8,066,657. In U.S. Pat. No. 8,066,657, an abdominal binder comprising a pocket affixed to the outside of the abdominal binder for holding one or more drainage bulbs is disclosed.

Although the disclosure discussed above solves the problem of securing the drainage reservoir by providing the pocket to hold the drainage reservoir, the patient may have to remove the abdominal belt as it absorbs water and the patient would have to keep the belt dry by removing it entirely or if worn in the shower, wait for the belt to dry before putting on clothing. Further, any adverse move by the patient may cause the drainage reservoir to loose suction required to receive the blood.

Other documents describing the closest subject matter provide for a number of more or less complicated features that fail to solve the problem in an efficient and economical way. None of these patents suggest the novel features of the present invention. Specifically, none of the disclosures in the art disclose an apparatus that is made up of a waterproof material and can be used to secure the drainage reservoir to the body of the patient; the apparatus facilitates reduction in loss of suction at the drainage reservoir.

Therefore, there is a need in the art for an apparatus to couple a drainage reservoir to a body of a patient, which helps to reduce the loss of suction at the drainage reservoir.

SUMMARY OF THE INVENTION

It is one of the main objects of the present invention to provide an apparatus to couple a drainage reservoir to a body of a patient and avoids the drawbacks of the prior art.

It is one object of the present invention to provide an apparatus to couple a drainage reservoir to a patient. The apparatus comprises a flat silicone like apparatus with a tab protruding out from the device with an orifice. The first end comprises an adhesive surface. Further, the apparatus includes a clip that couples to the orifice in the tab. Further, the clip is attached to the strap at the top of the drainage bulb. The first end of the device is attached to the body of the patient by an adhesive strip on the side facing the patient's body.

It is another object of the present invention to attach the apparatus to the body using an adhesive (similar to that of ostomy products) such that the patient can attach or remove the apparatus with ease. Typically, after surgery and while at the hospital or surgery center, the device is given to the patient while staying at the surgical facility during post operative rest immediately following surgery. The device is given to the patient along with the drain and attached to the patient prior to going home. Once there is no more need for the drain bulb, the device is easily removed from the body of the patient as it is no longer needed.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 illustrates a drain device 10, in accordance with prior art.

FIG. 5 illustrates a drainage reservoir 200 coupled to a body B of the patient with the help of the apparatus 100, in accordance with one embodiment of the present disclosure.

DETAILED DESCRIPTION OF THE EMBODIMENTS OF THE INVENTION

The following detailed description is intended to provide example implementations to one of ordinary skill in the art, and is not intended to limit the invention to the explicit disclosure, as one or ordinary skill in the art will understand that variations can be substituted that are within the scope of the invention as described.

The present disclosure discloses an apparatus to couple a drainage reservoir to a patient. The apparatus comprises a device having, a first end in a flat structure. Further, the device comprises a tab coupled to the first end. The tab comprises an orifice. The first end comprises an adhesion surface. Further, the apparatus includes a clip coupled to the orifice in the tab of the device. The first end of the device is coupled to the body of the patient, and the clip is coupled a drainage reservoir such that the drainage reservoir is coupled to the body of the patient with the help of the device, and the clip being attached to the strap of the drain bulb.

Various features and embodiments of an apparatus to couple a drainage reservoir to a body of a patient are explained in conjunction with the description of FIGS. 2-5.

Figure 2A:
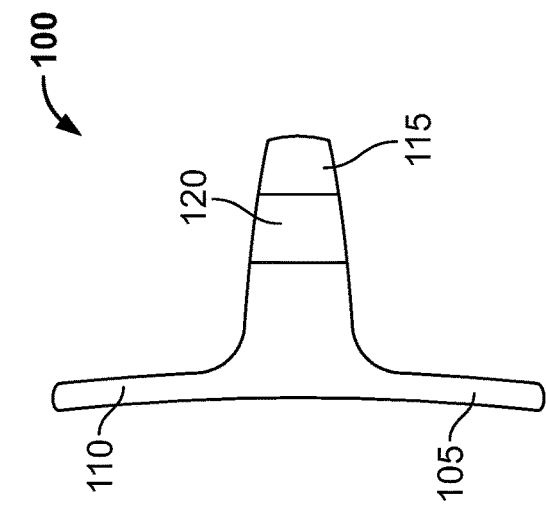
FIGS. 2, 2A and 2B illustrate a top view, a side view and a front view of an apparatus 100 for protecting or securing a drainage reservoir to a body of a patient, in accordance with one embodiment of the present disclosure.
Figure 2B:
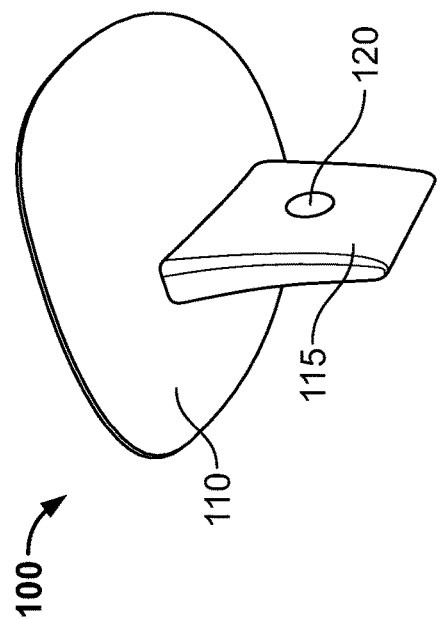
Figure 2:
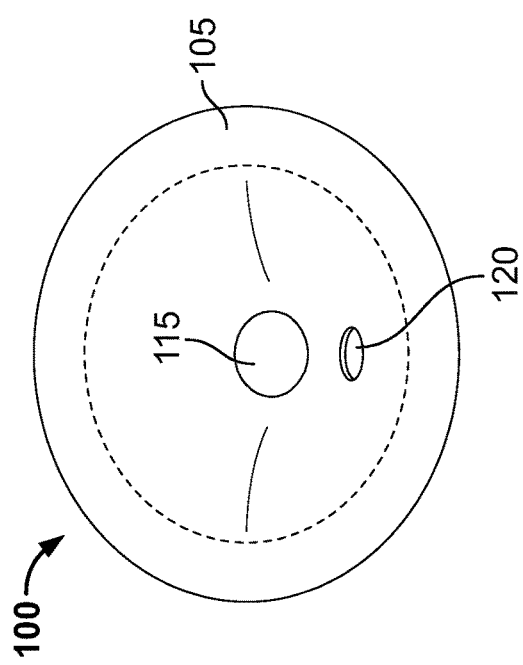

Referring to FIGS. 2, 2A and 2B, a top view, a side view and a front view of an apparatus 100 for coupling or securing a drainage reservoir to a body of a patient is shown, in accordance with one embodiment of the present disclosure. The apparatus 100 comprises a circular device 105. The device 105 will be made up of a synthetic material such as waterproof silicon rubber, polyvinyl chloride (PVC), polyurethane (PU). The device 105 comprises a first end 110 and a tab 115.

In one example, the first end 110 is provided in generally a flat surface 120. It should be understood that the present disclosure is explained considering that the first end 110 comprises the flat surface for illustrative purpose, however, it is obvious to a person skilled in the art to provide any structure at the top of the device 105. In one example, the first end 110 of the device 105 may be provided with an adhesive (surface). Further, the tab 115 may be provided in a tapered section indicating that size or width of the device 105 decreases progressively from the first end 110. It should be understood that the tab 115 protrudes from the device 105.

Further, the tab 115 comprises an orifice 120. The orifice 120 may indicate a hole in the tab 115.

Figure 3:
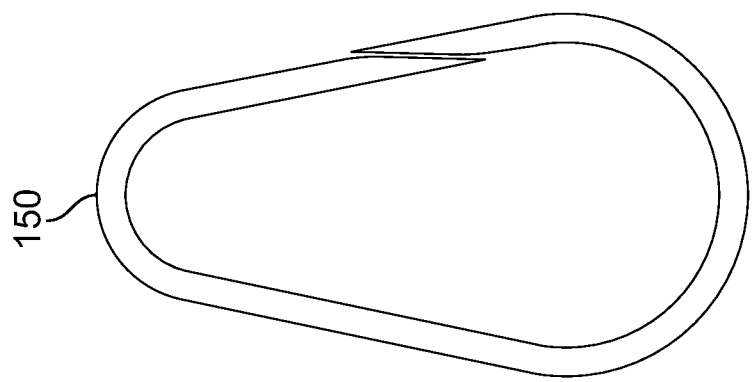
FIG. 3 illustrates a clip 150, in accordance with one embodiment of the present disclosure.

Referring to FIG. 3, a clip 150 is shown. The clip 150 will be made up of plastic material.

Figure 4:
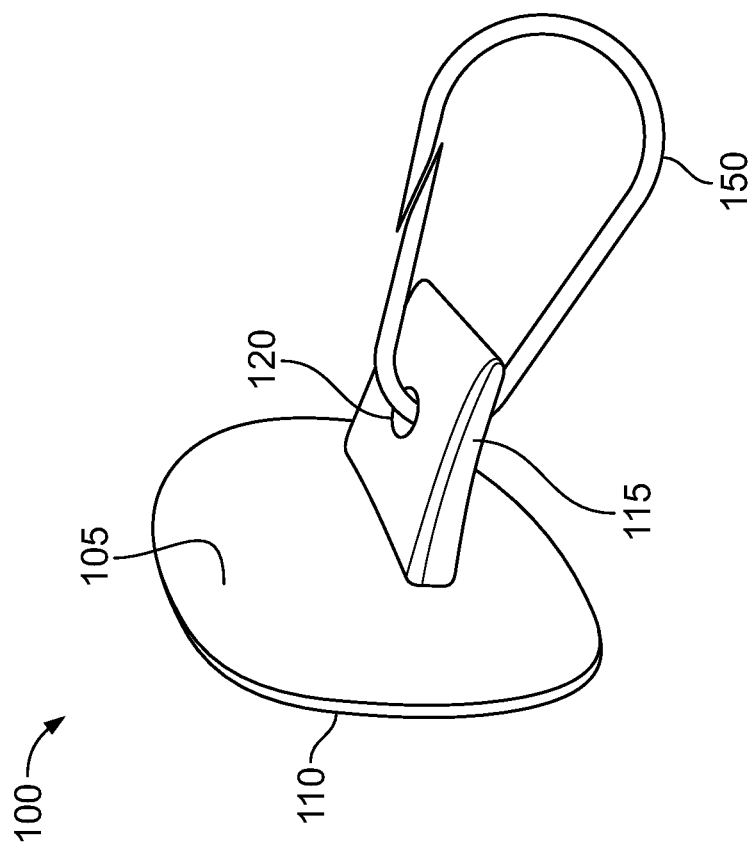
FIG. 4 illustrates the clip 150 coupled to the apparatus 100, in accordance with one embodiment of the present disclosure.

Referring to FIG. 4, the clip 150 inserted in the orifice 120 of the apparatus 100 is shown, in accordance with one embodiment of the present disclosure. It should be understood that when the clip 150 is received in the orifice 120, then the clip 150 is made to suspend or hang with the device 105.

Now referring to FIG. 5, a schematic diagram of the apparatus 100 used to couple a drain device to a body B of a patient is shown, in accordance with one embodiment of the present disclosure. The drain device may comprise a Jackson-Pratt drain or drain bulb or drainage reservoir or drainage bulb 200, a drain tube 205. As known the drain tube 205 is placed in a vicinity of a surgical site to aid in fluid removal. Typically this drain tube 205 is placed in surgery and secured by a strip 210 sterile dressing or bandage of some sort like a Tegaderm™.

The drain tube 205 will be made up of a plastic or any other suitable material. The length of the drain tube 205 may be chosen based on need or as per recommendation of a surgeon. The drainage reservoir 200 may be made up of transparent material. The drainage reservoir 200 may be used to carry fluids away from the surgical sites through the drain tube 205.

In accordance with one embodiment of the present disclosure, the drainage reservoir 200 is coupled to the body B of the patient with the help of the apparatus 100. As can be seen in FIG. 5, the apparatus 100 may be coupled to the body B of the patient. Specifically, the front end 110 of the device 105 is coupled to the body B. As explained above, the front end 110 of the device 105 comprises adhesive surface. As such, the device 105 gets attached to the body B of the patient. It should be understood that the patient might attach the device 105 to the body B at various places e.g., at the abdomen, waist and so on. After attaching the device 105 to the body B, the clip 150 may be inserted in the orifice of the tab protruding from the device 105.

As explained above, the drain device is provided near the surgical site. Specifically, the drain tube exits the surgical site. It should be understood that the drain tube is placed under the patient's skin during the surgery.

The device 105 is attached to the patient by adhesive. The clip 150 is attached to the device 105 by the orifice 120 in the protruding tab 115 on one end and the strap 175 of the drainage bulb on the other.

In one example, the drainage reservoir 200 may be directly coupled to the clip 150. In another example, the drainage reservoir 200 may be coupled to the clip 150 via the strap 175 as explained above.

As the drainage reservoir 200 is coupled to the body B with the help of the apparatus 100, any sudden twist or movement by the patient does not result in pulling the drain tube placed in the wound. As a result, the drain tube is not moved with respect to the movement of the body, the drainage reservoir 200 and the drain tube 205 as is the case when attached to clothing via a safety pin. As such, the suction created at the drainage reservoir 200 to receive the blood from the wound i.e., the drain tube to the drainage reservoir 200 is not affected and reduces chance of being pulled out of wound and need to reset suction.

It should be understood that the device may be attached anywhere on the body of the patient with the help of adhesive strip provided at the front end. Since, the device is attached to the body using the adhesive provided at its surface, there is no risk from a safety pin to body of the patient, or the drainage reservoir or the extension tube. Further, as the drainage reservoir is coupled to the body with the help of the apparatus described herein, the patient need not use his hands to hold the drainage reservoir. As such, the patient may use his both hands to perform variety of tasks e.g., taking a shower without having to hold the drainage reservoir and so on.

Based on the above, the apparatus allows eliminating the safety pin for pediatric patients when they have to use the drainage reservoir. Further, the apparatus described above is attached or secured to the drainage bulb once at the hospital or surgery center and it does not require any further detaching or reattaching until no longer needed at all. This particularly gives advantage over use of safety pin which requires detaching and reattaching every time a patient showers or changes clothing.

The apparatus as described above can be used to couple or secure the drainage reservoir to the body of the patient provided at hospital or surgery center immediately following surgery.

It should be understood that the apparatus might be provided in suitable size depending on size of the drainage reservoir or number of drainage reservoirs provided on the patient. Further, it should be understood that the drawings are provided for illustrative purpose and should not be construed in limited sense.

It is understood that the device being attached to the patient by the adhesive layer. The clip is attached to the device through the orifice in the tab protruding from the device and attached on the other end to the strap on the top of the drainage bulb itself.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An apparatus to couple a drainage reservoir to a body of a patient, the apparatus comprising:
   A) a support device having a rear side, wherein the rear side includes an adhesive thereon, the rear side having adhesive thereon is configured to be adhered to a user's skin;
   B) a tab centrally mounted to said support device, said tab protruding perpendicularly from a central portion of the support device, said tab being tapered towards a top end, wherein the tab includes a through hole that is centrally located and going entirely through a thickness of the tab, the through hole including dimensions that are adapted to receive and secure a carabiner or clip therein, wherein said tab is a rectangular one-piece structural member with a top side and a bottom side extending from the support device, wherein said orifice is disposed on the rectangular structural member, wherein said orifice is a circular opening extending entirely through the rectangular structural member from said top side to said bottom side; and
   C) a clip operatively coupled to the orifice, said clip being entirely closed when secured to said orifice, wherein the rear side of the support device is coupled to the body of the patient, and wherein the clip is used to couple the drainage reservoir such that the drainage reservoir is coupled to the body of the patient with the help of the support device and the clip, wherein said clip includes a diagonal slit formed thereon, wherein said drainage reservoir includes a strap, said strap is located on an outer lateral portion of said base of said drainage reservoir, said drainage reservoir is a bulb that suctions when squeezed, said strap being coupled to the clip through the diagonal slit, wherein an uppermost end of said clip is attached to said through hole of said tab, wherein a bottommost end of said clip is attached to said strap, said strap being located entirely below the tab, a drain tube and a strip, said strip entirely covers a wound, said strip is entirely above said drainage reservoir, the drain tube is attached to the drainage reservoir at one end and to the strip at the opposite end, by means of said clip the drainage reservoir is attached and disposed entirely below of said tab, the strip the support device and the drainage reservoir are disposed in a vertical arrangement.

2. The apparatus of claim 1, wherein the support device is made of a silicone or waterproof material.

3. A support apparatus, the apparatus consisting of:
   A) a support device including a rear side, wherein the rear side includes an adhesive thereon, said support device having rounded corners, wherein said support device is made of a silicone and waterproof material, the rear side having adhesive thereon is configured to be adhered to a user's skin proximal to a wound;
   B) a tab centrally mounted to said support device, said tab protruding perpendicularly from a central portion of the support device, said tab being tapered towards a top end, wherein the tab includes a through hole that is centrally located and going entirely through a thickness of the tab, the through hole including dimensions that are adapted to receive and secure a clip therein, wherein said tab is a rectangular structural member with a top side and a bottom side extending from the support device, wherein said through hole is disposed on the rectangular one-piece structural member, wherein said through hole is a circular opening extending entirely through a central portion of the rectangular structural member from said top side to said bottom side, wherein said through hole is tapered and decreases in height the further the orifice is away from the support device, wherein said through hole includes a width that is less than half a length of the tab; and
   C) a clip secured to the orifice, said clip being closed when secured to said orifice, said clip being tapered, wherein the support device is coupled to a body of a patient with said adhesive, a drainage reservoir, wherein said drainage reservoir is a bulb that suctions when squeezed, a strap, a drain tube and a strip, said strip entirely covers said wound, said strip is entirely above said drainage reservoir, the drainage reservoir is coupled to the clip with a strap, said strap is located on an outer lateral portion of said drainage reservoir, said drainage reservoir and said strap being entirely below said tab, thereby the drainage reservoir is coupled to the body of the patient with the help of the support device and the clip the drain tube is attached to the drainage reservoir at one end and to the strip at the opposite end, said strip being entirely above of said support device and said tab, wherein said clip includes a wide side and a narrow side, said narrow side being received within said orifice, said narrow side being in constant abutting contact with said orifice, said wide side being entirely below said tab and said narrow side, said wide side of said clip is attached to said strap, wherein said clip is a carabiner, said support device adhered on the user's skin is proximal to said wound covered by the strip, the support device is disposed below the strip and are separated by a predetermined distance, said support device is aligned with respect to said strip, said support device is greater in width than said strip, the strip the support device and the drainage reservoir are disposed in a vertical arrangement.

4. The apparatus of claim 1, wherein said through hole is tapered and decreases in height the further the orifice is away from the support device.

5. The apparatus of claim 1, wherein said through hole is located towards a front end of the tab.

6. The apparatus of claim 1, wherein said through hole is centrally located on said tab.

7. The apparatus of claim 1, wherein said support device includes rounded corners.

8. The apparatus of claim 1, wherein said through hole includes a width that is less than half a length of the tab.

9. The apparatus of claim 1, wherein said clip is tapered.

10. The apparatus of claim 1, wherein said clip includes a diagonal slit located about a circumference of said clip.

11. The apparatus of claim 1, wherein said clip includes a wide side and a narrow side, said narrow side being received within said orifice, said narrow side being in constant abutting contact with said orifice, said wide side being entirely below said tab and said narrow side.

12. The apparatus of claim 1, wherein said wound is entirely above said tab and said clip.

\* \* \* \* \*